US010265478B2

(12) United States Patent
Kouyoumjian et al.

(10) Patent No.: US 10,265,478 B2
(45) Date of Patent: Apr. 23, 2019

(54) INJECTION DEVICE

(75) Inventors: Garen Kouyoumjian, Leamington Spa (GB); Robert Veasey, Leamington Spa (GB); David Plumptre, Droitwich Spa (GB); Christopher Jones, Tewkesbury (GB); Catherine Anne MacDonald, Ashby-de-la-Zouch (GB); James May, Kenilworth (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 514 days.

(21) Appl. No.: 13/497,773

(22) PCT Filed: Sep. 29, 2010

(86) PCT No.: PCT/EP2010/064426
§ 371 (c)(1),
(2), (4) Date: Aug. 3, 2012

(87) PCT Pub. No.: WO2011/039233
PCT Pub. Date: Apr. 7, 2011

(65) Prior Publication Data
US 2012/0310206 A1 Dec. 6, 2012

(30) Foreign Application Priority Data
Sep. 30, 2009 (EP) .................................. 09171766

(51) Int. Cl.
*A61M 5/315* (2006.01)
*A61M 5/24* (2006.01)
*A61M 5/31* (2006.01)

(52) U.S. Cl.
CPC .... *A61M 5/31543* (2013.01); *A61M 5/31551* (2013.01); *A61M 5/31585* (2013.01);
(Continued)

(58) Field of Classification Search
CPC .......... A61M 5/31528; A61M 5/31551; A61M 5/31555; A61M 5/31543; A61M 5/31585
See application file for complete search history.

(56) References Cited

U.S. PATENT DOCUMENTS

| 533,575 A | 2/1895 | Wilkens |
| 4,865,591 A | 9/1989 | Sams |

(Continued)

FOREIGN PATENT DOCUMENTS

| CA | 2138528 | 12/1998 |
| CA | 2359375 A1 | 7/2000 |

(Continued)

OTHER PUBLICATIONS

Third Party Observation submitted in European Patent Application No. 10 766 250.4 dated Sep. 24, 2015.
(Continued)

*Primary Examiner* — Bhisma Mehta
*Assistant Examiner* — Hamza A Darb
(74) *Attorney, Agent, or Firm* — Fish & Richardson P.C.

(57) ABSTRACT

An injection device (1) for administering a fixed dose of a medication is provided. The injection device (1) comprises a housing (2) wherein a drive mechanism comprising a drive member (3) is at least partially enclosed and a dosing element (34) which is fixed relative to the drive member (3). Here, a dose can be set by rotating the dosing element (34) relative to the housing (2) in a dose set direction (105) and the dose can be dispensed by pushing the dosing element (34) towards the housing (2). Moreover, a method is provided for operating an injection device (1) for the administration of a fixed dose of a medication: A dose can be set by rotating a dosing element (34), a dose can be dispensed by pushing the dosing element (34) towards the housing (2) and
(Continued)

Figure 1:
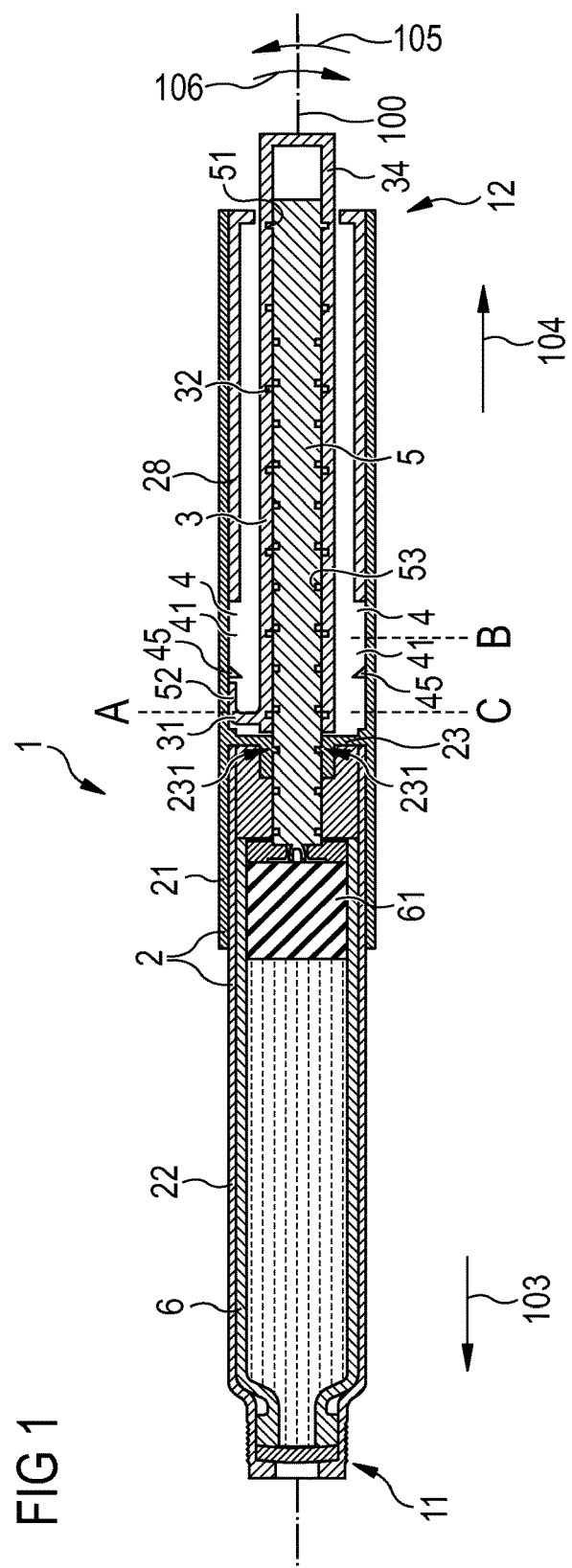

a dose can be cancelled by rotating the dosing element (34) in a direction (106) opposite to the dose set direction (105).

13 Claims, 10 Drawing Sheets

(52) U.S. Cl.
CPC .............. *A61M 5/24* (2013.01); *A61M 5/3129* (2013.01); *A61M 5/3156* (2013.01); *A61M 5/31525* (2013.01); *A61M 5/31541* (2013.01); *A61M 5/31558* (2013.01); *A61M 2005/2407* (2013.01); *A61M 2005/2488* (2013.01); *A61M 2205/581* (2013.01); *A61M 2205/582* (2013.01)

(56) References Cited

U.S. PATENT DOCUMENTS

| | | |
|---|---|---|
| 5,092,842 A | 3/1992 | Bechtold et al. |
| 5,226,895 A | 7/1993 | Harris |
| 5,226,896 A | 7/1993 | Harris |
| 5,279,586 A | 1/1994 | Balkwill |
| 5,304,152 A | 4/1994 | Sams |
| 5,320,609 A | 6/1994 | Haber et al. |
| 5,378,233 A | 1/1995 | Haber et al. |
| 5,383,865 A | 1/1995 | Michel |
| 5,391,157 A | 2/1995 | Harris et al. |
| 5,480,387 A | 1/1996 | Gabriel et al. |
| 5,505,704 A | 4/1996 | Pawelka et al. |
| 5,582,598 A | 12/1996 | Chanoch |
| 5,626,566 A | 5/1997 | Petersen et al. |
| 5,674,204 A | 10/1997 | Chanoch |
| 5,688,251 A | 11/1997 | Chanoch |
| 5,725,508 A * | 3/1998 | Chanoch et al. .............. 604/207 |
| 5,807,346 A | 9/1998 | Frezza |
| 5,820,602 A | 10/1998 | Kovelman et al. |
| 5,851,079 A | 12/1998 | Horstman et al. |
| 5,921,966 A | 7/1999 | Bendek et al. |
| 5,957,896 A | 9/1999 | Bendek et al. |
| 5,961,495 A | 10/1999 | Walters et al. |
| 6,004,297 A | 12/1999 | Steenfeldt-Jensen et al. |
| 6,193,698 B1 | 2/2001 | Kirchhofer et al. |
| 6,221,046 B1 | 4/2001 | Burroughs et al. |
| 6,235,004 B1 | 5/2001 | Steenfeldt-Jensen et al. |
| 6,248,095 B1 | 6/2001 | Giambattista et al. |
| 6,562,006 B1 | 5/2003 | Hjertman et al. |
| 6,613,023 B2 | 9/2003 | Kirchhofer et al. |
| 6,699,224 B2 | 3/2004 | Kirchhofer et al. |
| 6,899,698 B2 | 5/2005 | Sams |
| 6,932,794 B2 | 8/2005 | Giambattista et al. |
| 6,936,032 B1 | 8/2005 | Bush, Jr. et al. |
| 7,169,132 B2 | 1/2007 | Bendek et al. |
| 7,241,278 B2 | 7/2007 | Moller |
| 7,678,084 B2 | 3/2010 | Judson et al. |
| 7,850,662 B2 | 12/2010 | Veasey et al. |
| 8,186,233 B2 | 5/2012 | Joung et al. |
| 2002/0052578 A1 | 5/2002 | Moller |
| 2002/0120235 A1 | 8/2002 | Enggaard |
| 2003/0050609 A1 | 3/2003 | Sams |
| 2004/0059299 A1 | 3/2004 | Moller |
| 2004/0097883 A1 | 5/2004 | Roe |
| 2004/0210199 A1 * | 10/2004 | Atterbury .......... A61M 5/31566 604/224 |
| 2004/0267207 A1 | 12/2004 | Veasey et al. |
| 2005/0113765 A1 | 5/2005 | Veasey et al. |
| 2006/0153693 A1 | 7/2006 | Fiechter et al. |
| 2006/0178630 A1 * | 8/2006 | Bostrom .............. A61M 5/2066 604/135 |
| 2007/0016143 A1 | 1/2007 | Miller et al. |
| 2009/0054846 A1 | 2/2009 | Ulrich et al. |
| 2009/0275916 A1 | 11/2009 | Harms et al. |
| 2010/0094253 A1 * | 4/2010 | Boyd et al. .................... 604/506 |

FOREIGN PATENT DOCUMENTS

| | | |
|---|---|---|
| EP | 0496141 A1 | 7/1992 |
| EP | 0688571 A1 | 12/1995 |
| EP | 0897729 A2 | 2/1999 |
| EP | 0937471 A2 | 8/1999 |
| EP | 0937476 A2 | 8/1999 |
| EP | 1776975 A2 | 4/2007 |
| EP | 1923083 A1 | 5/2008 |
| EP | 1923084 A1 | 5/2008 |
| EP | 2201972 A1 | 6/2010 |
| WO | 9307922 A1 | 4/1993 |
| WO | 9324160 A1 | 12/1993 |
| WO | 9938554 A1 | 8/1999 |
| WO | 0110484 A1 | 2/2001 |
| WO | 0230495 A2 | 4/2002 |
| WO | 02092153 A2 | 11/2002 |
| WO | 03080160 A1 | 10/2003 |
| WO | 2004078239 A1 | 9/2004 |
| WO | 2004078242 A2 | 9/2004 |
| WO | 2005046770 A1 | 5/2005 |
| WO | 2006084876 A1 | 8/2006 |
| WO | 2008058665 A1 | 5/2008 |
| WO | 2009/039851 | 4/2009 |
| WO | 2009080775 A1 | 7/2009 |

OTHER PUBLICATIONS

English translation of Japanese Office Action for JP App. No. 2012-531397, dated Jul. 29, 2014.
Form PCT/IPEA/416, Notification of Transmittal of The International Preliminary Report on Patentability.
Office Action Issued in European Patent Application No. 10766250.4 dated Nov. 14, 2014.
International Search Report and Written Opinion in Application No. PCT/EP2010/064426, dated Mar. 21, 2011, 11 pages.
International Preliminary Report on Patentability in Application No. PCT/EP2010/064426, dated Feb. 10, 2012, 11 pages.
"Pen-injectors for medical use—Part 1: Pen-injectors—Requirements and test methods," International Standard, reference No. ISO 11608-1:2000(E), first edition Dec. 15, 2000, 32 pages.

* cited by examiner

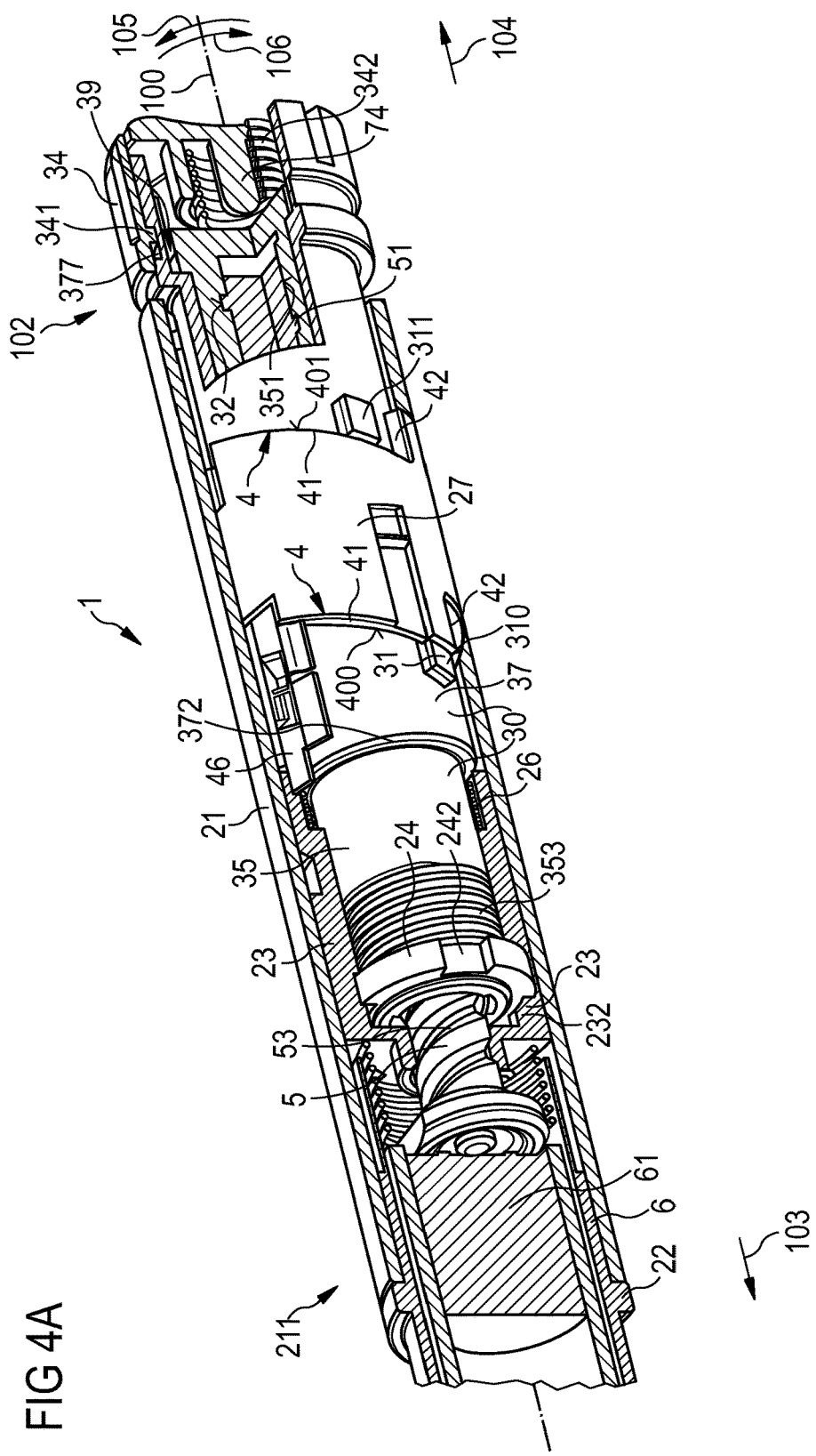

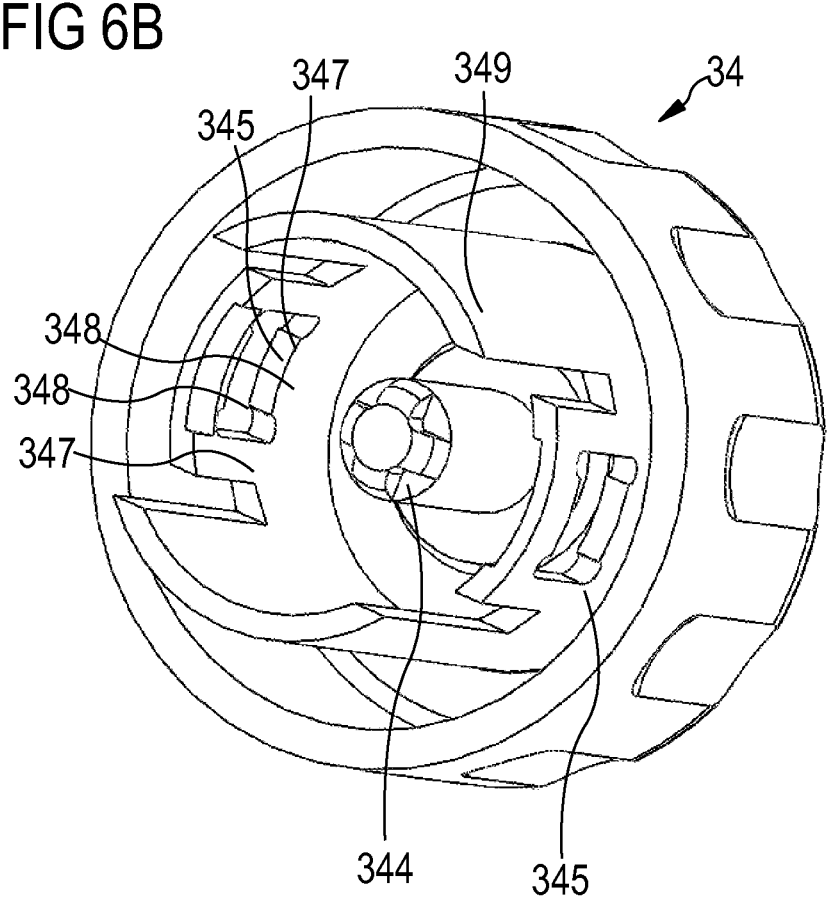

INJECTION DEVICE

CROSS REFERENCE TO RELATED APPLICATIONS

The present application is a 35 U.S.C. 371 National Application of PCT/EP2010/064426 filed Sep. 29, 2010, which claims priority to European Patent Application No. 09171766.0, filed Sep. 30, 2009, the entire contents of which are incorporated entirely herein by reference.

This disclosure relates to an injection device for administering a fixed dose of a medication. In particular, it relates to a drive mechanism for such an injection device.

The patent application EP 1 923 084 A1 discloses an injection device for setting and dispensing a fixed dose of a medicament. Here, in order to set a dose, a user pulls a dose button in a proximal direction and, in order to dispense the dose, pushes the dose button towards a distal direction of the injection device.

The publication WO 2004/078239 A1 discloses an injection device, wherein a user can select the size of a dose. In order to set a dose, the user rotates a dose dial sleeve with respect to a housing and, in order to dispense dose, a user depresses a dose button.

It is the aim of the present invention to provide an injection device for administering a fixed dose of a medication which is easy to use and highly reliable.

According to a first aspect of the present invention, an injection device for administering a fixed dose of a medication is provided.

In this context, the term "fixed dose" means that in such an injection device, a user does not have the option of varying the absolute size of a dose. Preferably, the absolute size of a dose to be dispensed is predetermined by the design of the drive mechanism of the device. Preferably, a dispensing of a medicament is only enabled when the dose is fully set, for example, when a dosing element is moved in a dose set direction until further movement in the dose set direction is disabled.

The injection device comprises a housing wherein a drive mechanism comprising a drive member is at least partially enclosed. Furthermore, the injection device comprises a dosing element. Preferably, the dosing element serves to actuate the drive member.

The injection device is configured such that a dose can be set by rotating the dosing element relative to the housing in a dose set direction and the dose can be dispensed by pushing the dosing element towards the housing. In this context, a "set operation" and "setting a dose" means that the drive mechanism is prepared for a subsequent dose dispense operation.

Preferably, the injection device is configured such that when a movement of the drive member is actuated by the dosing element, the movement of the dosing element is equal to the movement of the drive member. This means that the amount of movement and the direction of movement of the drive member equals the amount and direction of movement of the dosing element.

Thus, by operating the dosing element a corresponding movement of the drive member during a dose set and dose dispense operation is caused. Preferably, the dosing element directly acts on the drive member. As an example, the drive member may be actuated by the dosing element through abutting faces of the dosing element and the drive member.

Due to the direct interaction of the dosing element and the drive member the user has direct control over the movement of the drive member. Thereby, a reliable setting and dispensing of the dose may be achieved, while further error-prone mechanical processes, e. g. a mechanical coupling or decoupling of the dosing element and the drive member, can be omitted. In addition to that, additional components can be omitted and a cheaper production of the injection device may be achieved.

Preferably, the dosing element and the drive member are permanently engaged to each other during dose set and dose dispense operations.

Preferably, during dose set and dose dispense operations relative rotational and translational movements of the dosing element and the drive member are prevented. However, before or after dose set and dispense operations, a small relative translational movement or a small relative rotational movement of the dosing element and the drive member may be allowed. In particular, a small axial displacement of the dosing element and the drive member may be allowed during certain operation phases of the device for providing further functionality.

In one embodiment, the dosing element is permanently fixed relative to the drive member. In this case, during all operation phases of the device, a relative movement of the dosing element and the drive member is permanently prevented. Consequently, when a movement of the drive member is actuated by the dosing element, the movement of the dosing element equals the movement of the drive member.

As an example, the dosing element may be an integral part of the drive member.

This may be useful to further reduce the costs of producing the injection pen, because here, the dosing element and the drive member can be produced in the same production step. Furthermore, the injection pen may be more robust.

The dosing element may be formed by an end part of the drive member extending beyond the end of the housing, such that it can be gripped by a user. In order to improve the handling of the dosing element, the dosing element may be provided with a grip surface or may have a cross-section larger than the cross-section of the drive member.

In an alternative embodiment, the dosing element may be a separate component which is permanently fixed relative to the drive member.

This may be useful if a standard drive member is used in the injection device which cannot be conveniently gripped by a user. Furthermore, a dosing element which is a separate component can be altered relatively easily, e. g. a different coloured dosing element could be used to indicate a device with a different drug without having to change any mechanism components.

The drive member may be engaged with a piston rod acting on a piston in a cartridge wherein a medicament is disposed. Preferably, in a dose dispense operation, the movement of the dosing element and therewith the movement of the drive member towards the housing results in a movement of the piston rod towards the distal end of the injection device. Thereby, also the piston is moved forward and the medicament is pressed out of the cartridge. In this context, the term "distal direction" of the injection device denotes the direction pointing to the dispensing end of the device. The proximal direction is the direction opposite to the distal direction.

Preferably, the injection device provides a single dose set direction such that for every dose set operation, the direction of movement of the dosing element is identical.

Thereby, a simple and user-friendly operation of the injection device is provided.

In one embodiment, the movement of the dosing element during dose setting is not only rotational, but comprises an axial movement of the dosing element and the drive member away from the housing. Preferably, the dosing element carries out a movement along a helical path. In such an embodiment, both a pulling force on the dosing element and a rotational force in the dose set direction may result in the helical movement of the dosing element and, thus, in setting the dose. Thereby, also a user who is confused or not familiar with the injection device is able to set a dose just by acting on the dosing element without having to bear in mind if a rotational movement or a pulling movement of the dosing element is required.

In a preferred embodiment, in order to set a dose, the user acts on the dosing element and moves the dosing element from an initial position to a stop position relative to the housing. At the stop position, the dosing element can neither be pulled further out of the housing nor be rotated further in the dose set direction. When the dosing element has reached the stop position, the dose setting is completed. At the stop position, a user may push the dosing element towards the housing until an end position is reached, whereby during this movement the medicament is dispensed.

In a preferred embodiment, a set dose can be cancelled by rotating the dosing element in a direction, the so-called "dose unset direction", opposite to the dose set direction.

Here, the dose may be cancelled when the dose setting has been completed and the stop position has been reached. The dose may also be cancelled from a position of the dosing element between the initial position and the stop position. Preferably, in order to cancel the dose, the dosing element is rotated in a direction opposite to the dose set direction until the initial position is reached again.

This functionality may be particularly useful for a user who is not familiar with the injection device and, e.g., is trained to operate the injection device. Here, medical staff may wish to demonstrate to the user how the pen operates by setting a dose and cancelling the dose several times without having to expel any medicament. Furthermore, this may also be useful when a user after having set the dose decides that he wants to take the dose some time later and therefore, wishes to deselect the dose. This can not be achieved in an injection device wherein the only action available to the user after the dose has been set is to depress the dose button to expel the dose.

The injection device may comprise an indicator to indicate to the user the two options after the dose has been set, i.e. dispensing the dose by pushing the dosing element or cancelling the dose by rotating the dosing element backwards. The indicator may be printed on the drive member and visible through an aperture in the housing.

In a preferred embodiment, the relative movement between the drive member and the housing is defined by a track.

In particular, the track may be provided on the drive member, the housing or a component fixed to the housing. Preferably, one or more engaging features on the housing, a component fixed to the housing or on the drive member is guided along the track. Thereby, the relative movement of the drive member relative to the housing is restricted to a movement of the engaging feature along the track.

In one embodiment, the housing may have an inner track which engages with an engaging feature of the drive member. As one example, the track may be formed by a recessed path, wherein the engaging feature is guided. As a second example, the track may be formed by a path protruding from the inner surface of the housing. Here, the drive member may comprise two sets of engaging features enclosing the track and thus, being guided along the track.

Alternatively, the drive member may have an outer track which engages with an engaging feature of the housing. In particular, the drive member may comprise a recessed or a protruding path guiding one or more engaging features on the housing or on a component fixed to the housing.

In the following, it is assumed that the drive member has an engaging feature which engages with an inner track of the housing. However, the following description also encloses other embodiments, for example, embodiments wherein the drive member comprises an outer track engaging with an engaging feature of the housing.

When a user acts on the dosing element in order to set a dose or to dispense a dose, the engaging feature travels along the path of the track. Preferably, the engaging feature is guided by the path of the track such that a movement of the drive member relative to the housing has to be in compliance with the path of the track. Here, the position of the dosing element relative to the housing may be defined by the position of the engaging feature relative to the associated track. As the user has direct control over the drive member, he may directly control the relative movement of the engaging feature along the path of the track. Thereby, the risk is reduced that the engaging feature locks in the track, e.g., due to high levels of friction or contamination from debris entering the device.

In one embodiment, the housing has a longitudinal axis and the path of the track oscillates between two confining positions at the longitudinal axis.

In this context, a confining position is defined by a plane being perpendicular to the longitudinal axis. Here, when following the path of the track, the track runs towards one of the confining positions and then changes its direction and runs towards the second confining position. Thus, along the longitudinal axis, the path of the track is confined to a region between the two confining positions. The path of the track may reach the confining positions or may change its direction before a confining position is reached. In particular, for example when the injection device is configured such that subsequent doses differ, the positions at which the track changes its direction from a distal to a proximal direction or vice versa may vary along the track.

Accordingly, the track comprises both sections running in the distal direction and sections running in the proximal direction of the housing. This means that, when following the track in one direction relative to the track, at specific sections of the track, the direction of the movement along the track at least partially points into the proximal direction or into the distal direction of the housing, respectively.

The track may comprise several consecutive identical segments, which are arranged one after another in a consecutive order. In particular, the identical segments may be only shifted by a certain amount of rotation around the longitudinal axis and thus differ only in their angular positions around the longitudinal axis.

In a further embodiment, the track comprises only one segment.

Preferably, each segment corresponds to a process of dose setting and dose dispensing.

The drive member may comprise two or more engaging features each engaging with a different segment of the track of the housing. The engaging features may be arranged at symmetric positions around a longitudinal axis. As an example, two diametrically opposite engaging features may be guided by one segment of the track each. In this case, the engagement of the drive member with the housing may be more robust and the risk for disengagement or locking may be reduced.

In a preferred embodiment of the segments of the track, each segment comprises a dose set section being inclined against the longitudinal axis and a dose dispense section being less inclined against the longitudinal axis than the dose set section.

Preferably, when the user rotates the dosing element in the dose set direction in order to set a dose, the engaging feature travels along the dose set section in the dose set direction. The dose set section may extend from a first position towards a second position which is further away from the distal end, thereby running helically around the longitudinal axis along the dose set direction. Preferably, the first position corresponds to the initial position of the dosing element and the second position to the stop position of the dosing element.

Preferably, the dose dispense section starts at the end of the dose set section and extends towards a third position, wherein the third position is located closer towards the distal end than the second position. In one embodiment, the third position is located at the same position relative to the longitudinal axis as the first position and has an angular offset relative to the first position. When a user pushes the dosing element towards the housing the engaging feature moves from the second position to the third position of the track at the housing. Preferably, the inclination of the dose dispense section against the longitudinal axis is such that the dosing element carries out a mainly translational movement along the axis when the user pushes the dosing element.

In a preferred embodiment, the dose dispense section runs in a direction parallel to the longitudinal axis.

Here, the action of pushing the dosing element results in a mainly translational movement of the dosing element relative to the housing. This may be very convenient for the user as he does not feel a rotational movement of the dosing element when pushing the dosing element.

In other embodiments, the dose dispense section may run in a direction not purely parallel to the longitudinal axis. Thereby, the mechanical advantage of the movement of the dosing element and the movement of the piston inside the cartridge may be improved.

In a preferred embodiment, during cancelling a dose, the engaging feature of the drive member travels along the dose set section in a direction opposite to the dose set direction. Here, the dose set section has the double function of setting and cancelling the dose. When a user during the setting of the dose or at the end of the setting process decides that he does not want to expel the dose, he may rotate the dosing element towards the opposite direction. Thereby, the engaging feature of the drive member travels along the dose set section in a backward direction.

In one embodiment, the injection device comprises a feedback element, which gives an audible or tactile signal when one of the dose setting and the dose dispense operation has been completed.

As an example, for this aim, the injection device may comprise a detent.

The detent may be located at the track of the housing and precede the dose dispense section in the dose set direction. The detent may interact with the engaging feature of the drive member, whereby an audible and tactile signal is given. As an example, the detent may be an element fixed at the track of the housing, extending into the path of the track.

The detent may comprise a flexible or an inflexible protrusion. Additionally or alternatively, the engaging feature may comprise a flexible part. In a preferred embodiment, when the engaging feature is moved against the detent, the engaging feature may overcome the detent due to a flexible deformation of one or both of the detent and the engaging feature. The audible and/or tactile feedback may result from the mechanical resistance of the elements when pushed against each other or from the snapping back of one or both of the elements after the engaging feature has passed the detent.

In alternative embodiments, the detent may be positioned at a distance further away from the track. Here, it may interact with a part of the drive member which extends from the engaging feature or a separate part of the drive member. The detent and the interacting element are located such that the interaction results in an audible and/or tactile feedback when the engaging feature reaches the dose dispense section.

In one embodiment, the injection device comprises a non-return feature which at a predefined relative position of the housing and the drive member allows a relative movement of the drive member and the housing in one direction and prevents a relative movement in the opposite direction.

As an example, such a non-return feature may allow a movement of the engaging feature of the drive member along the dose set section and prevents a backward movement along the dose dispense section.

The non-return feature may be located at the end of the dose dispense section. Similar to the detent feature, the non-return feature may be a protrusion extending into the path of the track of the housing. It may have a lead-in such that at the end of the dose dispense section, a further movement of the engaging feature in the same direction is supported. Coming from the other direction, the non-return feature may have a stop face, such that the movement of the engaging feature in the backward direction along the dose dispense section is prevented.

In a further embodiment, the non-return feature may be located just after the start of the dispense section of the track to prevent users from delivering a partial dose and then cancelling the dose.

In an embodiment, where a cancelling of the dose is not supported, the non-return feature may prevent a movement of the dosing element in a direction opposite to the dose set direction at the end of a dose set operation. Here, the non-return feature may be located at the end of the dose set section.

The non-return feature may also be located at the housing or at a position further away from the track and may engage with a separate element of the drive member as long as the interaction takes place when the engaging feature has passed the dose dispense section.

In a preferred embodiment, each segment of the track takes up an angular range of 60°, 72°, 90°, 120° or 180°.

Preferably, the angular range of a segment is chosen such that a dose setting and a dose dispensing movement of the dosing element can be conveniently carried out by a user. With an angular range of 180°, the user has to rotate the dosing element about half a turn and then has to push the dosing element.

In a preferred embodiment, the track is closed in itself. Accordingly, the track is configured to form a continuous circuit.

Thereby, when starting from a specific location on the track and following the track in one direction, the starting location is reached again. In this embodiment, the track is configured such that, in principle, an arbitrary number of doses can be dispensed.

Here, preferably, the angular range of a segment is an integral fraction of 360°. In this case, the consecutive segments complete a full turn along the inner diameter of the housing and join up after the full turn.

In case that the dispensing of only a few doses of a medicament is required, the track may be terminated at its end. Here, the track may take up an angular range of less than 360°.

Preferably, a piston rod is provided, the piston rod acting on a piston disposed in a cartridge wherein the medicament is contained. In a preferred embodiment, the piston rod carries out a combined rotational and translational movement, for example, a helical movement, during dispensing the dose.

In one embodiment, the drive member is a drive member which at least partially encloses the piston rod. In particular, the drive member may have the shape of a sleeve.

The piston rod may be threadedly engaged with the drive member.

Preferably, the injection device is configured such that during dispensing the dose the amount of axial displacement of the piston rod differs from the amount of axial displacement of the drive member. In particular, during a dose dispense operation, the drive member may move mainly or purely axially relative to the housing, while the piston rod may carry out a helical movement relative to the housing. During a dose set operation, the drive member may carry out a helical movement relative to the housing and relative to the piston rod.

The drive member may have an inner thread which engages with an engaging feature of the piston rod. As a further example, the drive member may comprise an engaging feature engaging with an outer thread of the piston rod.

In the following, it is assumed that the drive member has an inner thread which engages with an engaging feature of the piston rod. However, the following description encloses also embodiments, wherein the drive member comprises an engaging feature engaging with an outer thread of the piston rod.

Preferably, the lead of the inner thread of the drive member equals the lead of the dose set section of the inner track of the housing. Thereby, when the dosing element and the drive member are helically moved out of the housing to set a dose, the inner thread of the drive member carries out a helical movement relative to the piston rod, while the piston rod itself remains stationary relative to the housing. During dose dispense, the drive member carries out a mainly translational movement relative to the housing in the direction towards the distal end. By the threaded engagement of the drive member with the piston rod, the movement of the drive member results in a movement of the piston rod.

The ratio of the amounts of movement along the longitudinal axis of the injection device of the drive member and the piston rod depends on the mechanical advantage of the device.

Preferably, the amount of axial displacement of the piston rod is smaller than the amount of axial displacement of the drive member.

Preferably, the piston rod is threadedly engaged with the housing. As an example, the piston rod may have a thread on its outer surface wherein a protrusion on the housing or on a component fixed to the housing is engaged. As an example, the piston rod may be threadedly engaged with a nut, which is fixed to the housing. In particular, the piston rod may be a double-threaded lead screw.

In one embodiment, the injection device comprises a stop feature which prevents one of a dose set or a dose dispense operation of the dosing element after the last available dose has been dispensed.

As an example, the stop feature may be configured as a last dose nut being threadedly engaged with the drive member. In particular, when the last dose of the medicament has been dispensed, the last dose nut may have reached the end of its threaded engagement with the drive member. At this point of operation, the last dose nut will block the first drive member such that a further dose set operation is prevented.

In a different embodiment, the inner thread of the drive member comprises a stop face which prevents the full setting of a dose after the last available dose has been dispensed.

Thereby, when a user tries to set a dose after the last available dose has been dispensed, the engaging feature of the piston rod may abut against the stop face of the inner thread of the drive member. As the piston rod is engaged with the housing, a counterforce is exerted on the drive member such that a further movement of the drive member in the dose set direction and the full setting of a further dose is prevented.

In a further embodiment, in the case that the piston rod is threadedly engaged with the housing, a further dose dispense operation may be prevented by a stop face on a thread provided on the piston rod.

In a preferred embodiment, the injection device is a pen-type device. As an example, the cartridge may contain medicaments like heparin, GLP1 or insulin.

In one embodiment, the device may be a reusable device, where a replacement of a medicament container and a re-usage of the device with a new medicament container are enabled. In this case, the drive mechanism may be resettable. In particular, the drive mechanism may be configured such that a resetting of the piston rod towards an initial position, which may be a most proximal position of the piston rod, is allowed.

For this aim, the drive member may be configured as a drive unit comprising a first drive member and a second drive member. During dose set and dose dispense operations, the first and second drive member may be locked to each other such that relative rotational movements between the first and second drive member are prevented. During these operations, the functionality of the drive member and the interaction with other elements of the device may be as described above. During a reset operation, a relative rotational movement between the first and second drive member may be allowed. The drive mechanism may comprise locking means configured to rotationally lock the first and second drive member in a dispense operation and configured to allow unlocking for enabling a resetting of the piston rod. Preferably, the unlocking takes place during the reset operation.

Furthermore, a method of operating an injection device for administering a fixed dose of a medication is disclosed. The method comprises the following steps, wherein the steps directly follow one after another. First, a dose is set by rotating a dosing element relative to a housing of the injection device in a single dose set direction of the injection device. Next, the dosing element is pushed towards the housing. Preferably during or at the end of the step of rotating the dosing element, the dose can be cancelled by rotating the dosing element in a direction opposite to the dose set direction.

The term "medicament", as used herein, preferably means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(w-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser- Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39), wherein the group -Lys6-NH2 may be bound to the C-terminus of the Exendin-4 derivative;

or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O)25, Asp28] Exendin-4(1-39)-Lys6-NH2,
H-desAsp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;

or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Other features will become apparent from the following detailed description when considered in conjunction with the accompanying drawings.

Figure 2:
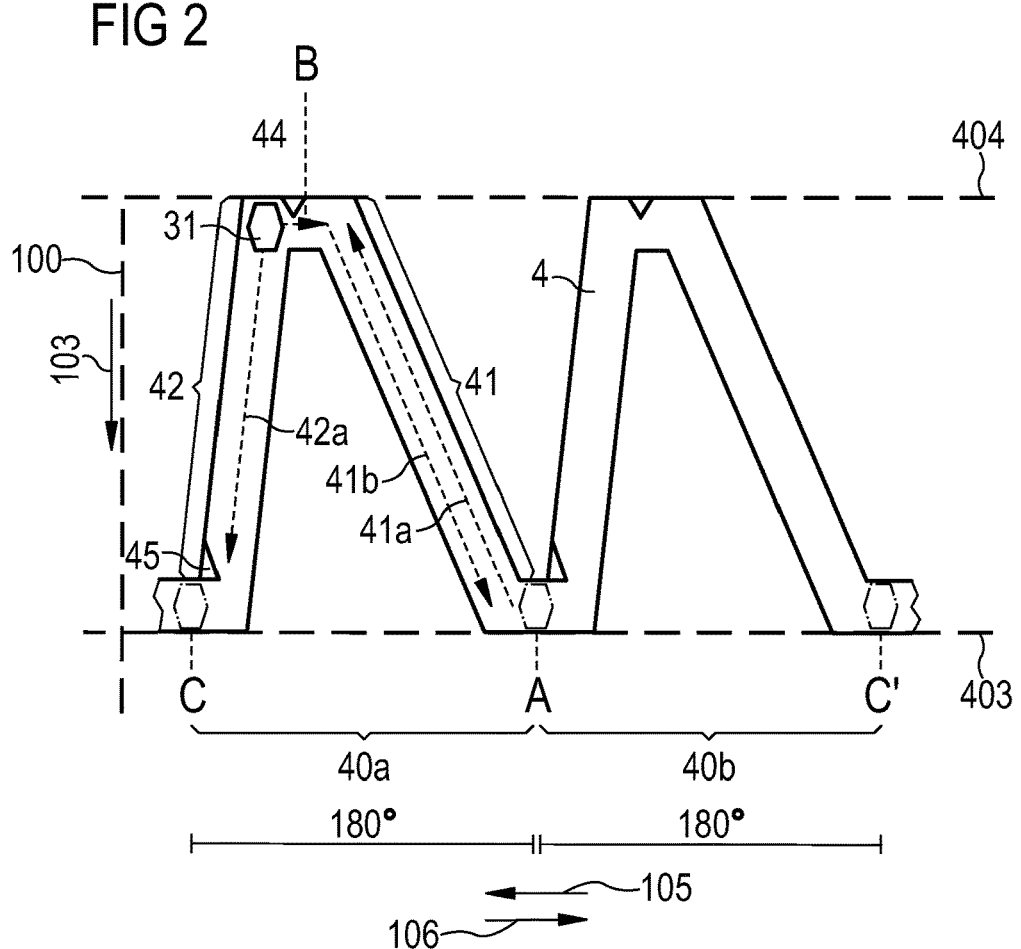
Figure 3:
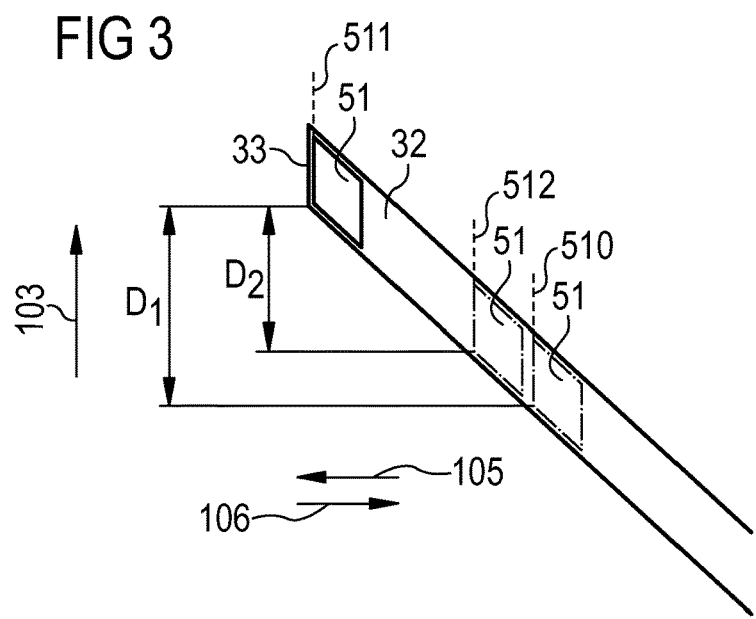
Figure 4B:
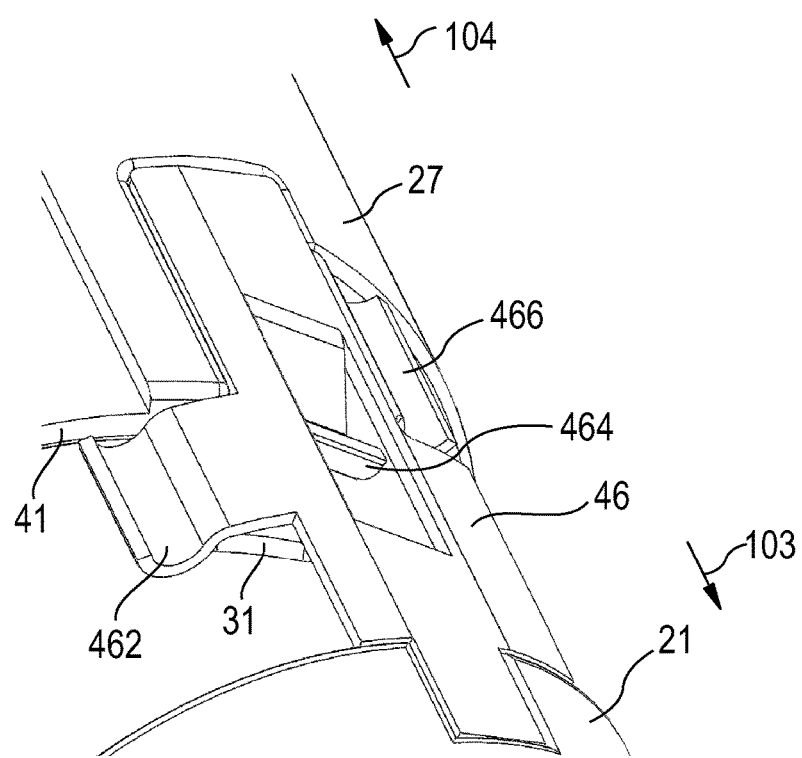
Figure 4C:
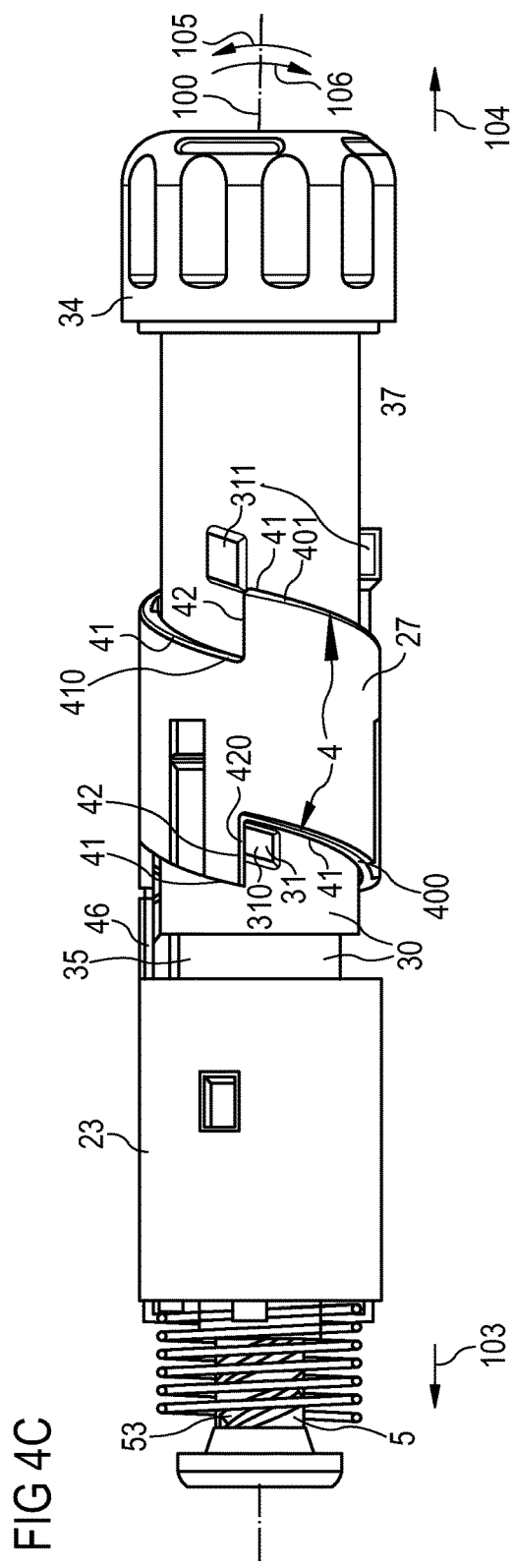
Figure 5A:
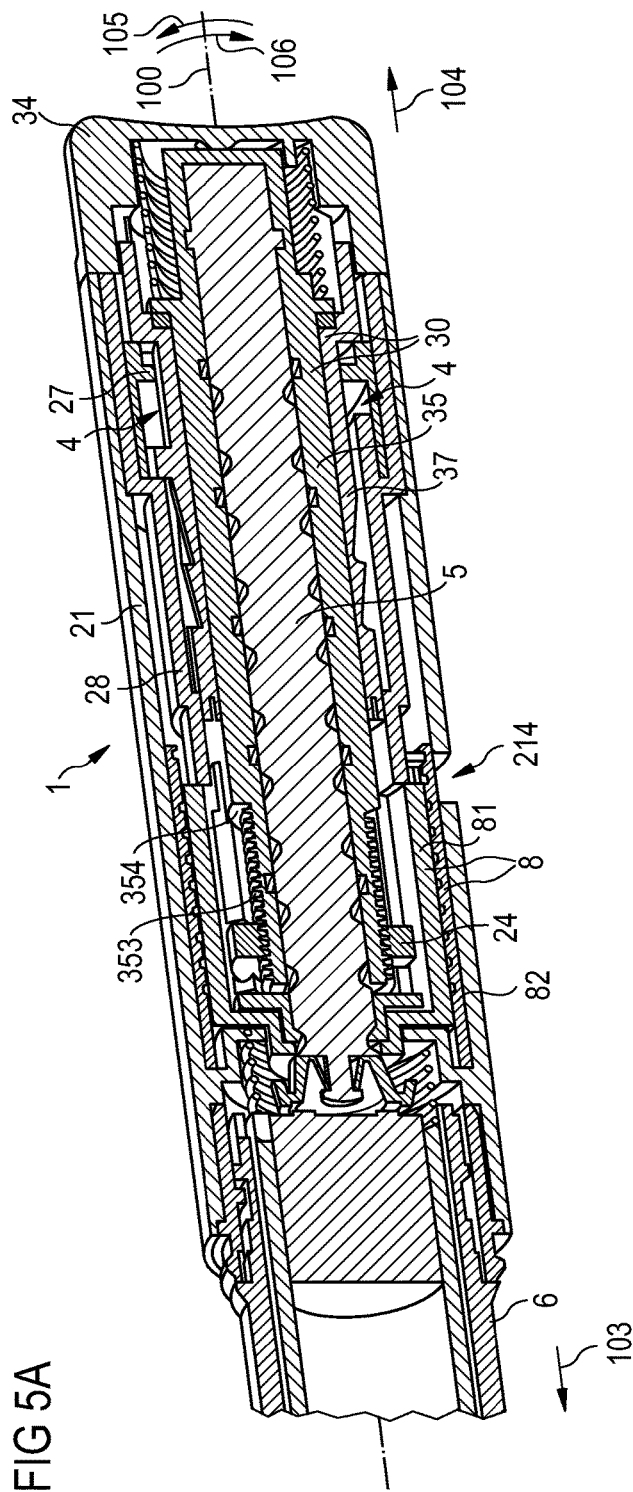
Figure 5B:
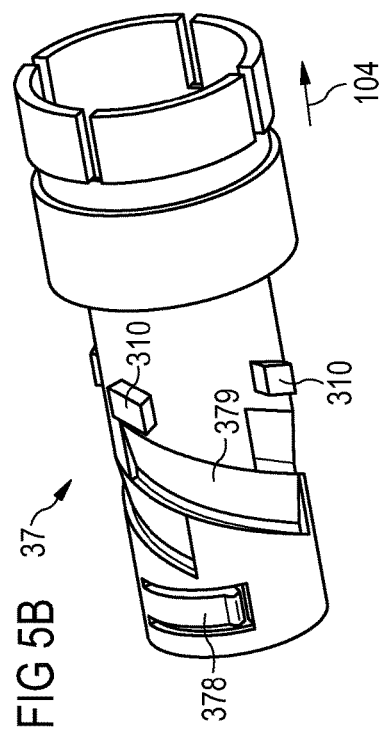
Figure 6A:
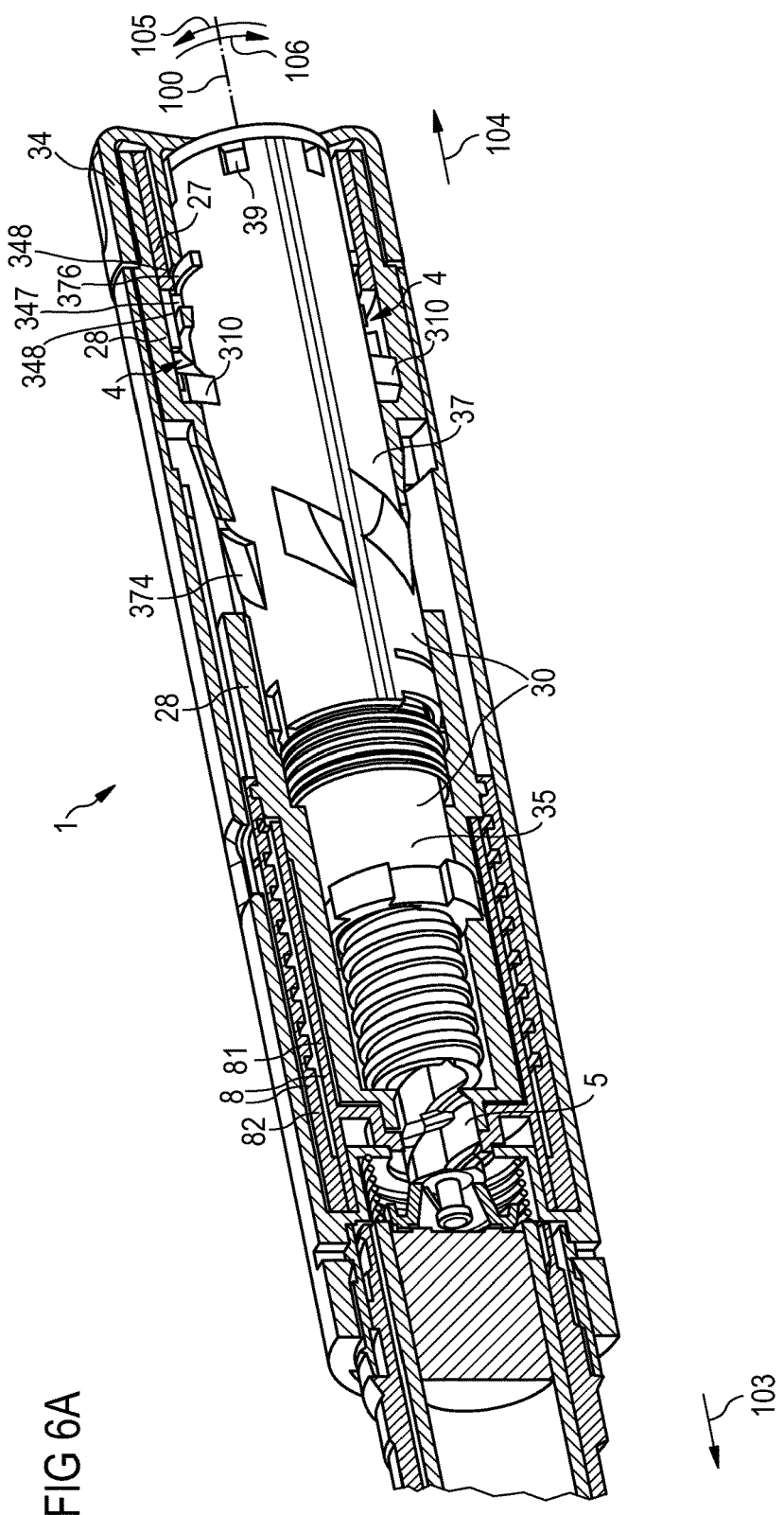
Figure 7A:
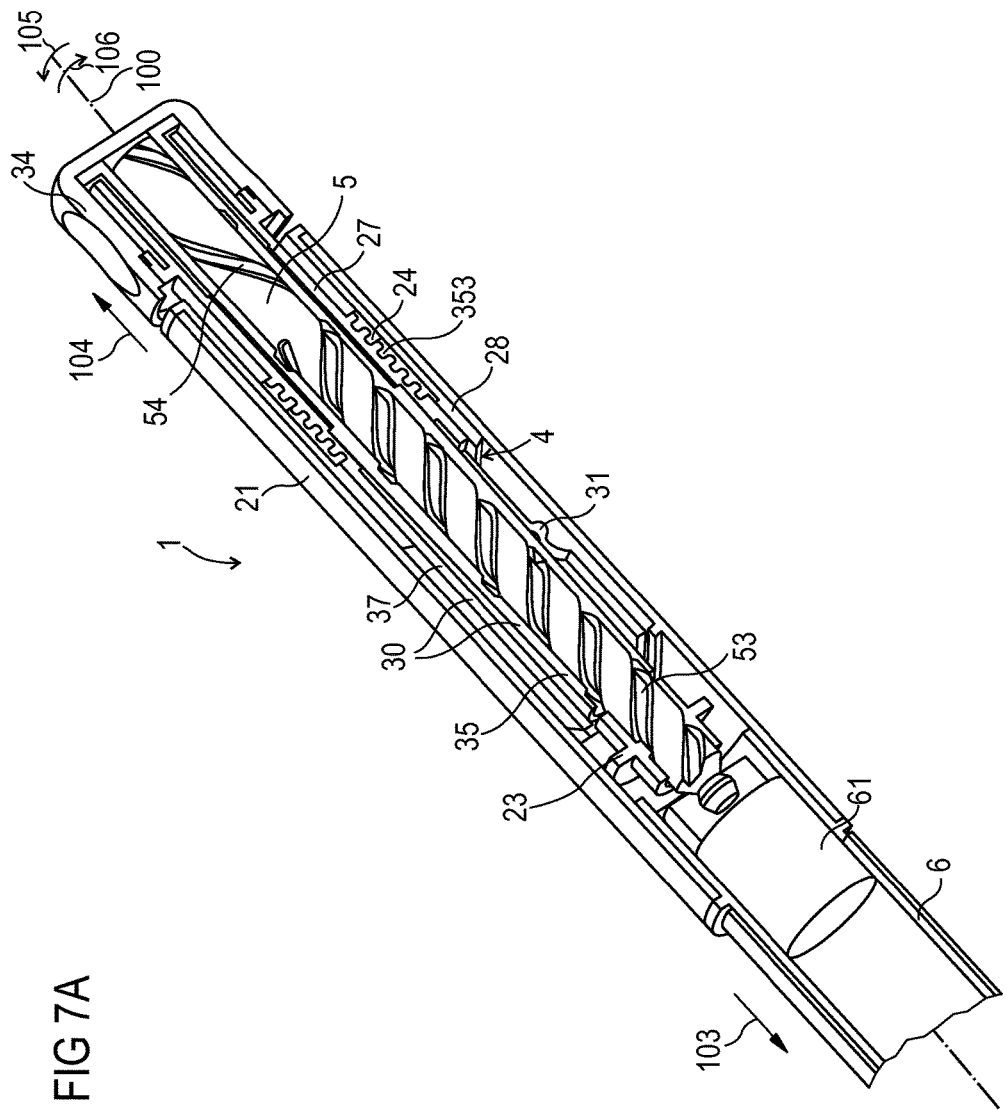
Figure 7B:
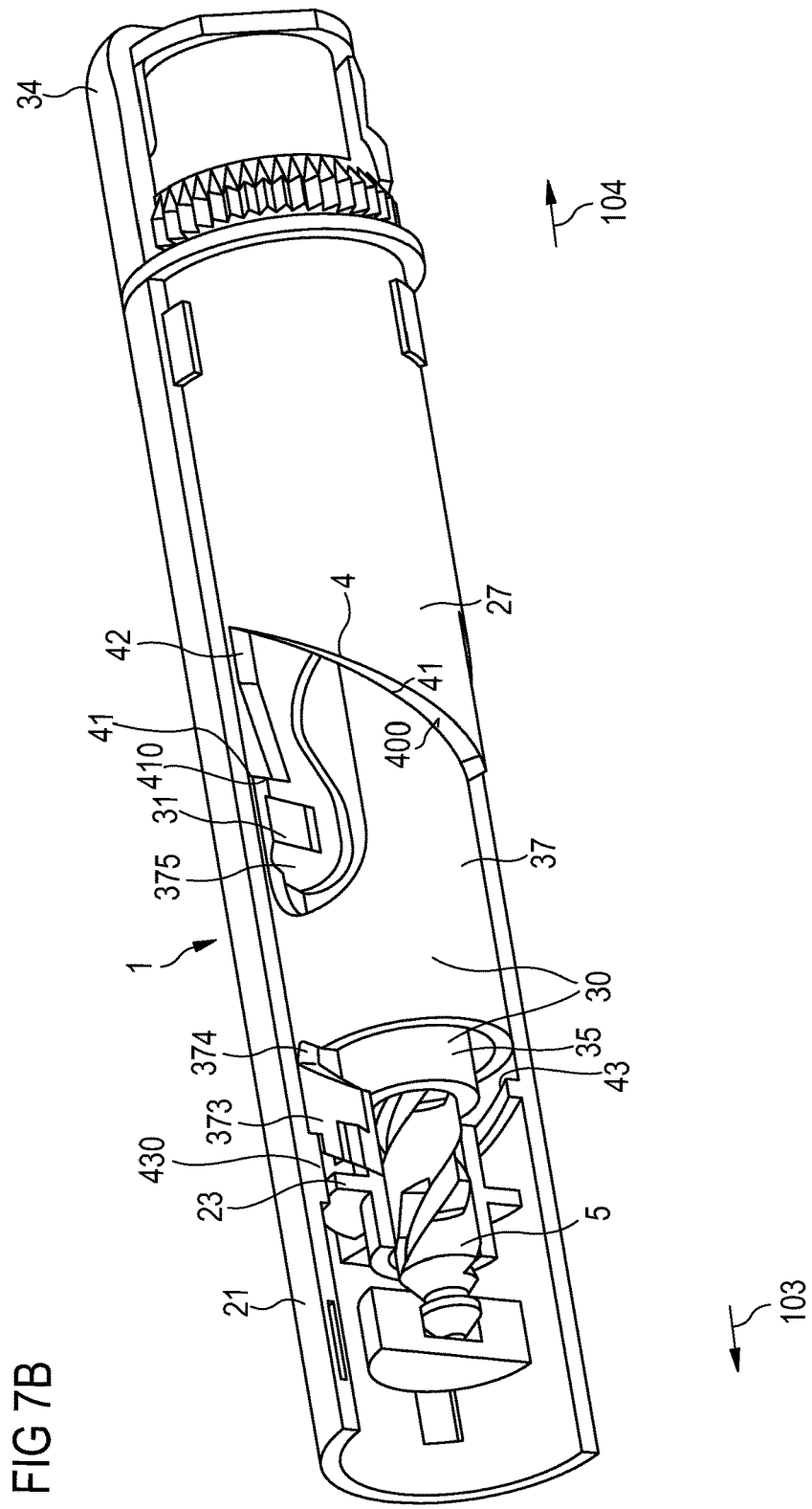

FIG. 1 is a cross-sectional view of a first embodiment of an injection device comprising a drive mechanism, FIG. 2 is a rolled-out depiction of an inner track on the housing engaged with an engaging feature of the drive member, FIG. 3 is a rolled-out depiction of an inner track on the drive member engaged with an engaging feature on the piston rod, FIG. 4A is a cut-away view of a second embodiment of an injection device, FIG. 4B is a detailed perspective view of an insert spring of the second embodiment, FIG. 4C is a perspective view of the dispense mechanism of the second embodiment of the injection device at the end of a dose set operation, FIG. 5A is a perspective cross sectional view of a third embodiment of an injection device, FIG. 5B is a perspective view of a drive member of the third embodiment of the injection device, FIG. 6A is a cut-away view of a fourth embodiment of an injection device, FIG. 6B is a perspective view of a dosing element of the fourth embodiment of the injection device, FIG. 7A is a cut-away view of a fifth embodiment of an injection device, FIG. 7B is a cut-away view of the drive mechanism of the fifth embodiment of the injection device.

FIG. 1 shows a pen-type injection device 1 having a longitudinal axis 100. The injection device 1 comprises a housing 2 with a main part 21 and a cartridge holder 22 wherein a cartridge 6 containing a liquid medicament is disposed. A needle unit (not shown here) can be attached to the distal end 11 of the injection device 1. The main housing 21 partially encloses a drive mechanism comprising a drive member 3 in the form of a drive sleeve partially enclosing a piston rod 5. The piston rod 5 acts on a piston 61, whereby during a movement towards the distal end 11 the medicament is pressed out of the cartridge.

At the proximal end 12 of the injection device 1, the drive member 3 extends beyond the main housing 21 such that the dosing element 34 formed by the end of the drive member 3 can be gripped by a user. Thereby, a user may set, dispense or cancel a fixed dose of a medicament.

The drive member 3 is engaged with the housing 2. The main housing 21 comprises an inner track 4, wherein an engaging feature 31 of the drive member 3 is guided. In particular, the track 4 is formed on the inner surface of the main housing 21 between a body insert 28 fixed to the main housing 21 and a nut 23 fixed to the main housing 21. The inner track 4 on the main housing 21 runs around the longitudinal axis 100.

The piston rod 5 is threadedly engaged with the drive member 3. The drive member 3 comprises an inner thread 32 engaged with an engaging feature 51 of the piston rod 5. In addition to that, the piston rod 5 is threadedly engaged with the main housing 21. For this aim, the piston rod 5 comprises an outer thread 53, wherein an engaging feature 231 of the nut 31 fixed to the main housing 21 is guided. Thus, the piston rod 5 is a double-threaded lead screw.

In order to set a dose, a user grips the dosing element 34 and rotates the dosing element 34 in a dose set direction 105, resulting in a helical movement of the dosing element 34 and the drive member 3 away from the housing 2 in the proximal direction 104. The position of the dosing element 34 and the drive member 3 relative to the housing 2 is defined by the position of the engaging feature 31 of the drive member 3 relative to the inner track 4 of the housing 2. Starting from an initial position A, the engaging feature 31 moves helically towards a stop position B. Thereby, also the dosing element 34 moves from its initial position A to its stop position B. Due to the design of the inner track 4 of the housing 2 and the inner thread 32 of the drive member 3, during the setting of the dose, the piston rod 5 remains stationary relative to the housing 2.

At the stop position B, a user can dispense the dose by pushing the dosing element 34 in the distal direction 103 towards the distal end 11 of the device 1 until an end position C is reached. During this movement of the dosing element 34 and the drive member 3, a force is exerted on the piston rod 5 by the threaded engagement of the piston rod 5 with the drive member 3 and the nut 31 fixed to the main housing 21. Thus, the piston rod 5 moves helically towards the distal end 11 and pushes the piston 61 forward. Thereby, the medicament is pressed out of the cartridge 6. The velocity ratio of the injection device 1 is defined by the ratio of the amount of axial displacement of the drive member 3 to the amount of axial displacement of the piston rod 5 during dispensing the dose. The velocity ratio depends on the ratio of the lead of the inner thread 32 of the drive member 3 to the lead of the outer thread 53 of the piston rod 5 and can be used to define the mechanical advantage of the mechanism.

Instead of pushing the dosing element 34 from the stop position B to the end position C and thereby dispensing the dose, the user may also cancel the set dose by twisting the dosing element 34 in a direction 106 opposite to the dose set direction 105. Also here, during cancelling the dose, the piston rod 5 remains stationary relative to the main housing 21.

FIG. 2 shows the inner track 4 of the main housing 21, wherein the engaging feature 31 of the drive member 3 is guided. The path of the inner track 4 runs around the inside diameter of the housing 2. For an illustrative purpose it is shown rolled out flat here. Relative to the longitudinal axis 100, the path of the track 4 is confined to a region between two confining positions 403, 404.

The inner track 4 completes a full turn such that the positions C and C' coincide. The inner track 4 comprises two consecutive identical segments 40a and 40b each taking up an angular range of 180°. Each segment 40a, 40b comprises a dose set section 41 and a dose dispense section 42. During a setting of the dose, the engaging feature 31 of the drive member 3 travels along the dose set section 41 from the initial position A towards the stop position B, and thereby moves helically around the longitudinal axis 100 of the injection device 1 in the dose set direction 105. The lead of the dose set section 41 is equal to the lead of the inner thread 32 of the drive member 3. Therefore, the piston rod 5 does not move relative to the housing 2 during the dose setting process. When the engaging feature 31 of the drive member 3 has arrived at the stop position B, the dose setting process is completed. A detent 44 is located at the stop position B which gives an audible or tactile signal when the engaging feature 31 passes the detent 44. The engaging feature 31 has a flexible part (not shown here) which flexes backwards when pushed against the detent. By the interaction of the detent 44 with the engaging feature 31, a user is informed that the dose has been set. Thereby, the user can decide if he wants to dispense the dose or cancel the set dose.

For dispensing the dose, at the stop position B, the user pushes the dosing element 34 towards the distal end 11 of the injection device 1. Thereby, the engaging feature 31 follows the path of the dose dispense section 42 until it reaches the end position C. By this movement, the piston rod 5 is also moved towards the longitudinal direction and thereby, a medicament is pressed out of the cartridge 6. In this embodiment, the dose dispense section 42 runs in a direction not purely parallel to the longitudinal axis I. At the end of the dose dispense section 42, a non-return feature 45 is located. The engaging feature 31 can pass the detent feature 45 when moving from the stop position B towards the end position C. However, the engaging feature 41 cannot pass the non-return feature 45 when moving in the opposite direction.

At the position B, instead of pushing the dosing element 34 in order to dispense the dose, a user may cancel the dose by rotating the dosing element 34 in a direction 106 opposite to the dose set direction 105. Thereby, the engaging feature 31 travels backwards along the path of the dose set section 41 from the stop position B towards the initial position A. During this movement, the drive member 3 moves along a helical path in the distal direction 103 of the injection device 1, while the piston rod 5 remains stationary relative to the housing 2.

After a cycle of dose setting and dose dispensing has been carried out, a user may set and dispense a new dose, wherein the engaging feature 31 is now guided by the consecutive segment 40b. Thus, multiple fixed doses of a medicament may be dispensed.

In a further embodiment of the injection device 1, the drive member 3 may comprise two engaging features, wherein one of the engaging features travels in the segment 40a and the other one in the segment 40b during a dose setting and dose dispense cycle.

Moreover, the device 1 may comprise a non-return feature just after the start of the dispense section 42 to prevent users from delivering a partial dose and then unselect the dose by pushing the dosing element in the proximal direction 104, whereby the engaging feature 31 moves backwards on the dispense section 42.

FIG. 3 shows an embodiment of the inner thread 32 of the drive member 3 guiding the engaging feature 51 of the piston rod 5. The path of the inner thread 32 runs along the inside diameter of the drive member 3. For an illustrative purpose, it is shown rolled out flat here.

The inner thread 32 of the drive member 3 comprises a stop face 33, which, after the last available dose has been dispensed, prevents the full setting of a further dose.

Before the last dose has been set, the engaging feature 51 of the piston rod 5 is located at the position 510 relative to the drive member 3. While the last dose is being set, the drive member 3 rotates out of the housing 2 on a helical path, while the piston rod 5 remains stationary relative to the housing 2. Thereby, relative to the inner thread 32 of the drive member 3, the engaging feature 51 of the piston rod 5 moves towards the position 511. In this position 511, the engaging feature 51 is adjacent to the stop face 33, but does not prevent the setting of the dose. When the dose is being dispensed, the piston rod 5 moves towards the distal end 11 of the injection device 1. After the dose has been dispensed, the engaging feature 51 of the piston rod 5 is located at the position 512 relative to the drive member 3. Due to the threaded engagement of the piston rod 5 with the drive member 3 and the housing 2, the axial displacement D1-D2 of the piston rod 5 relative to the housing 2 is smaller than the axial displacement D1 of the drive member 3.

If a user tries to set a subsequent dose, the drive member 3 can carry out the axial displacement D2 relative to the piston rod 5 before the engaging feature 51 of the piston rod 5 abuts the stop face 33. This is insufficient to set a dose, because a full dose setting would require the axial displacement D1. Hence, the full dose can not be set. The ratio of the axial displacement D1 to that of the axial displacement D2 depends on the mechanical advantage of the injection device 1. In particular, where the drive member 3 moves axially relative to the housing 2 during dispense, the velocity ratio is equal to the ratio D1/(D1−D2). Thus, for a velocity ratio of 3:1, the distance D2 is equal to two thirds of the setting distance D1 and for a velocity ratio of 2:1, the distance D2 is equal to half of the setting distance D1. The velocity ratio can be defined in order to produce a mechanical advantage in the mechanism.

FIGS. 4A, 4B, 5A, 5B, 6A, 6B, 7A and 7B show further embodiments of injection devices. Here, during a dose dispense operation the piston rod 5 is driven by a drive unit 30 comprising a first 35 and a second drive member 37. During set and dispense operations, the first 35 and second drive member 37 are locked to each other such that relative movements between the first 35 and second drive member 37 are prevented.

In the embodiments according to FIGS. 4A to 6, the first drive member 35 can be unlocked from the second drive member 37 in order to allow a resetting of the piston rod 5 to an initial position when replacing an empty cartridge 6. In the embodiments according to FIGS. 7A and 7B, the first drive member 35 can be unlocked from the second drive member 37 in order to allow a priming of the device 1 prior to the delivery of the first dose of the medicament.

In all embodiments, the first and the second drive member are locked to each other during dose set and dispense operations such that the drive unit can be regarded as a single drive member. In particular, the various features of the injection devices shown in FIGS. 4A to 7B, for example the design of the track, a last dose nut, a dose counter, a feedback element or a non-return feature are equally applicable to injection devices where the drive member can not be split into two parts.

FIG. 4A shows a second embodiment of an injection device 1, in particular a pen-type injection device, for setting and dispensing fixed doses of a medicament. The injection device 1 is a reusable multi-dose device allowing subsequent administering of doses from a cartridge 6 and allowing a replacement of the cartridge 6. The assembly and operation of this embodiment during dose set and dispense operations is similar to that described above. The reference numerals indicate features with the same or similar function.

The drug delivery device 1 comprises a main housing 21, which at least partially encloses a drive mechanism of the device 1 and extends along a longitudinal axis 100. At the distal end 211 of the main housing 21, a cartridge holder 22 containing a cartridge 6 filled with a liquid medicament is releasably attached. As examples, the medicament may comprise GLP-1 or heparin. The cartridge holder 22 is screwed onto the main housing 21 of the device 1. In further embodiments, a cartridge holder may have a bayonet connection with a main housing.

The cartridge 6 comprises a piston 61 which, for dispensing the medicament, is pushed by a piston rod 5 in the distal direction 103, whereby the medicament is pressed out through a needle (not shown here) at the distal end of the cartridge holder 22. In particular, the piston rod 5 acts on the piston 61 via a bearing 56 located at its distal end. In a dose dispense operation, the piston rod 5 is driven by a drive unit 30 comprising a first 35 and a second drive member 37. During a dose set and dispense operation, the first drive member 35 is rotationally and translationally locked to the second drive member 37 by clutch means 39.

The piston rod 5 has the shape of a double-threaded lead screw extending along the longitudinal axis 100 of the device 1. In particular, the piston rod 5 comprises a female outer thread 53 running from its distal end to its proximal end, engaged with a nut 23 fixed to the main housing 21. Furthermore, at its proximal end, the piston rod 5 comprises engaging features 51, threadedly engaged with a female inner thread 32 on the first drive member 35.

At its proximal end 102, the device 1 comprises a dosing element 34 operable by a user. The element 34 has the shape of a button protruding out of the proximal end of the main housing 21. For setting a dose of the medicament, the dosing element 34 is rotated relative to the main housing 21 in a dose set direction 105, whereby the dosing element 34 carries out a helical movement out of the main housing 21. For dispensing the set dose, the dosing element 34 is pushed in the distal direction 103. If a user, after having set a dose, decides not to dispense the dose, the set dose can be unset by rotating the dosing element 34 in a dose unset direction 106 opposite to the dose set direction 105, whereby the dosing element 34 carries out a helical movement towards the main housing 21.

The dosing element 34 is fixed to the second drive member 37 such that a relative rotational movement of the dosing element 34 and the second drive member 37 is prevented and a limited axial movement is allowed. In particular, the dosing element 34 comprises a lug 341 being guided in a short axial groove 377 on the outer surface of the second drive member 37. Thereby, a rotational movement of the dosing element 34 during dose setting causes an equivalent movement of the second drive member 37. On an axial movement of the dosing element 34 during dose dispense, the dosing element 34 first carries out a small axial movement relative to the second drive member 37 until the lug 341 abuts a distal end face of the groove 377. Then, on further pushing the dosing element 34 towards the main housing 21, the dosing element 34 acts on the second drive member 37, thereby pushing the second drive member 37 in the distal direction 103 during a dose dispense operation.

The first drive member 35 and the second drive member 37 have the shapes of hollow cylindrical sleeves extending along the longitudinal axis 100. The first drive member 35 is inserted into the second drive member 37.

In order to maintain the clutched engagement during a dose set and dispense operation, a spring 342 is located inside the dosing element 34, being compressed between an inner face at the proximal end of the dosing element 34 and an outer face at the proximal end of the first drive member 35. Thereby, the spring 342 exerts an axial force in the distal direction 103 on the first drive member 35, pressing the first drive member 35 towards the second drive member 37. Moreover, the dosing element 34 comprises an internal boss 344 which extends in an axial direction and comes into contact with the outer face of the first drive member 35 on a further compression of the spring 342. This helps to maintain the clutched engagement in a dose dispense operation.

The device 1 comprises a track 4, wherein two sets of protrusions 310, 311 on the outer surface of the second drive member 32 are guided during set and dispense operations. The two sets of protrusions serve as engaging features for engaging the drive unit 30 with the track 4. Thereby, the relative movement of the drive unit 3 and the main housing 21 is defined by and confined to the possible movement of the sets of protrusions 310, 311 along the track 4. In particular, the track 4 is provided by contact faces 400, 401 on the distal and proximal ends of a body insert 27 fixed to the main housing 21. The body insert 27 has the shape of a hollow sleeve, surrounding the second drive member 37. The first set of protrusions 310 runs along the distal contact face 400 and the second set of protrusions 311 runs along the proximal contact face 401.

The track 4 comprises several dose set 41 and dose dispense sections 42. The dose dispense sections 42 run in an axial direction, while the dose set sections run helically relative to the main hosing 21. During setting a dose, each set of protrusions 310, 311 runs along a dose set section 41 of the track 4. Thereby, the set of protrusions 310, 311 and thus, also the drive unit 3, carry out a helical movement relative to the main housing 21. During dose dispense, the protrusions 310, 311 run along a dose dispense section 42 of the track 4. Thereby, the drive unit 3 carries out an axial movement in the distal direction 103.

An insert spring 46 is located at the track 4, providing feedback to a user at specific points of operation and preventing a backwards movement of a protrusion 31 of the first set of protrusions 310 on a dose dispense section 42, after a dose has been dispensed.

FIG. 4B shows a detailed view of the insert spring 46 in the device 1 after a dose has been dispensed. The insert spring 46 is rigidly mounted between the housing 21, the insert 27 and the nut 23. The insert spring 46 features radial spring surfaces 462, 464, 466, that are disposed to interfere with a protrusion 31. The insert spring 46 comprises two radial spring surfaces 462, 466 which are arranged to deflect radially when deformed by the protrusion 31 and, thereby, after the completion of a dose set and dose dispense operation provide audible and tactile feedback to the user. The spring surface 462 indicating the start of a dose set operation also stops the second drive member 37 from sliding up the dose set section 41 without user input.

Another surface 464 is arranged to provide a non-return or unidirectional feature that permits the axial travel of the protrusion 31 in the distal direction 103 but prevents a travel in the proximal direction 104. Thereby, after a dose dispense operation, a backwards movement of the protrusions 31 along a dose dispense section 42 is prevented.

Furthermore, returning to FIG. 4A, a back-off spring 26 is rigidly mounted between the nut 23 and the second drive member 37 and abuts a distal face 372 of the second drive member 37. At the end of a dose dispense operation the back-off spring 26 is compressed by the second drive member 37 such that the back-off spring 26 produces an axial counterforce on the drive member 37 in the proximal direction 104. Thereby, after a dose dispense operation a small movement of the second drive member 37 can be triggered, causing a small movement of the piston rod 5 in the proximal direction 104. This allows a backing-off of the piston 61 in the proximal direction 104, whereby a dripping of the medicament can be prevented after the dose has been dispensed.

Moreover, the axial load produced by the back-off spring 26 leads to a small movement of the protrusion 31 in a proximal direction 104, whereby the protrusion 31 is pushed onto a tilted surface of the insert spring. This results in a small rotational movement of the second drive member 37 such that the sets of protrusions 310, 311 contact the subsequent dose set section 42.

Moreover, the drug delivery device 1 comprises a last dose nut 24, being threadedly engaged with a last dose thread 353 on the distal end of the first drive member 35. At its outer surface, the last dose nut 24 comprises notches 242 engaged with axial splines 232 on the nut 23. Thereby, a movement of the first drive member 35 in the dose set direction 105 will result in a movement of the last dose nut 24 along the last dose thread 353 in the proximal direction 104. When the last dose of the medicament has been dispensed, the last dose nut 24 will have reached the end of its threaded engagement with the first drive member 35. Here, the last dose nut 24 will block the first drive member 35 such that a further dose set operation is prevented.

FIG. 4C shows the dispense mechanism of the injection device 1 according to FIG. 4A at the end of a dose set operation. During setting a dose, the two sets of protrusions 310, 311 have traveled along a helical dose set section 41 of the track 4. When the protrusions 310, 311 have reached the end of a dose set section 41, the first set of protrusions 310 abuts stop faces 420 on the subsequent dose dispense section 42 preventing a further rotational movement in the dose set direction 105. Now, the user can choose between dispensing the dose by pushing the dosing element 34 in the distal direction 103 and unsetting the dose by twisting the dosing element 34 in the dose unset direction 106 opposite to the dose set direction 105.

During dose dispense, the two sets of protrusions 310, 311 run along an axial dose dispense section 42, whereby the drive unit 30 moves axially in the distal direction 103.

Thereby, the threaded engagement of the first drive member 35 with the piston rod 5 causes a distal movement of the piston rod 5 through its threaded engagement with the nut 23. This axial displacement is transmitted to the bung 61 in the cartridge 6 and results in a dispense of medicament from the cartridge 6.

The differences in pitch of the thread 53 on the piston rod 5 engaged with the nut 23 and the inner thread 32 on the first drive member 35 engaged with the piston rod 5 results in a ratio reduction between the axial displacement of the piston rod 5 relative to the axial displacement of the drive unit 30 during dose dispense. Thereby, a mechanical advantage is achieved.

During dose dispense, the two sets of protrusions 310, 311 move along the dose dispense sections 42 until the second set of protrusions 311 reaches a stop face 410 on a subsequent dose set section 41. Thereby, a further axial movement of the drive unit 3 in the distal direction 103 is prevented.

Furthermore, at the end of its axial travel along the track 4, a protrusion 31 on the second drive member 37 travels underneath the non-return feature of the insert spring 46. This provides feedback to the user that the dose dispense operation has been completed and ensures that the second drive member 37 cannot be pulled axially back up the dose dispense section 42 of the track 4.

FIG. 5A shows a third embodiment of an injection device 1 having a drive unit 30 comprising a first drive member 35 and a second drive member 37 which are rotationally and axially locked during dose set and dispense operations and allow an unlocking for resetting the piston rod 5.

In this embodiment, the insert spring has been removed and its functionality has been distributed among other parts of the device 1. Furthermore, a dose counter 8 indicating the number of remaining doses, which equals the number of remaining dose dispense operations, has been added.

In particular, the dose counter 8 comprises a number sleeve 82, carrying markings on its outer surface. The marking representing the current filling state of the cartridge 6 is visible through an opening 214 in the main housing 21. Here, also a marking may be provided indicating that a priming operation is required after resetting the device 1 or indicating that the cartridge 6 is empty.

The number sleeve 82 is driven by a rotational movement of the piston rod 5. The number sleeve 82 has a threaded engagement with an inner body 28 fixed to the main housing 21 and a splined engagement with a collar 81. The collar 81 is coupled to the main housing 21 such that a relative translational movement between the collar 81 and the housing 21 is prevented and a relative rotational movement is allowed. The collar 81 has a splined engagement with the piston rod 5 such that when the piston rod 5 carries out a rotational movement, the collar 81 equally rotates. Due to its splined engagement with the number sleeve 82, a rotation of the piston rod 5 also causes a helical movement of the number sleeve 82 through its threaded engagement with the inner body 28. The markings on the number sleeve 82 are printed over a helical path on the outer surface of the number sleeve 82 so that after a dose dispense operation the next marking appears in the opening 214.

The pitch of the thread 83 on the number sleeve 82 engaged with the inner body 28 can be selected such that the axial advancement of the number sleeve 82 is smaller or larger than the axial advancement of the piston rod 5. This allows all the required numbers to be printed on the number sleeve 82 in a legible size and allows minimizing the length of the number sleeve 82.

Moreover, the first drive member 35 has been modified such that the last dose nut 24 abuts against a stop face 354 on the first drive member 35 at the end of its threaded engagement with the piston rod 5. Thereby, a damaging of the end of the last dose thread 353 or a bump-over of the last dose nut 24 over the end of the last dose thread 353 can be prevented.

In this embodiment, the track 4 is provided by a channel formed between the inner body 28 and a body insert 27. The body insert 27 is permanently and rigidly fixed to the inner body 28. This allows a reduction of the size of the device 1.

FIG. 5B shows some key features of the second drive member 37 of the device 1 according to FIG. 5A. At its outer surface, the second drive member 37 comprises only one set of protrusions 310 guided in the track 4 for setting and dispensing doses of medicament.

Furthermore, the second drive member 37 has flexible arms 378 acting on detent features on the inner surface of the inner body 28, thereby providing user feedback at the start and the end of a dose set operation. Furthermore, the second drive member 37 has a series of helical sweep recesses 379 around its outer diameter having steps between each other. The recesses 379 interact with flexible arms on the inner body 28 providing user feedback and a non-return ratchet when the flexible arms click over a step at the end of a dose dispense operation.

FIG. 6A shows a fourth embodiment of an injection device 1 having a drive unit 30 comprising a first drive member 35 and a second drive member 37. During dose set and dose dispense operations the first drive member 35 is rotationally and translationally locked to the second drive member 37 by clutch means 39.

Also in this embodiment, the device 1 comprises a dose counter 8 comprising a number sleeve 82 being driven by a collar 81. The number sleeve 82 is threadedly engaged with an inner body 28. At its outer surface, the second drive member 37 comprises only one set of protrusions 310 being guided along a track 4 formed by a channel between an inner body 28 and a body insert 27.

On its outer surface, the second drive member 37 comprises ribs 376 for interaction with stop faces 77, 78 on the dosing element 34. Thereby, a limited relative rotational movement of the dosing element 34 and the second drive member 37 is allowed while a relative translational movement is prevented.

Moreover, the second drive member 37 comprises diamond-shaped protrusions 374 interacting with flexible arms on the inner body 28. Thereby, both a non-return feature and a feedback element providing the user with feedback at the end of a dose set and dispense operation are provided.

In this embodiment, by the modified design of the second drive member 37, the mouldability of the second drive member 37 is improved.

FIG. 6B shows the dosing element 34 of the device 1 of FIG. 6A. The dosing element 34 comprises an internal boss 344 which together with a spring (not visible here) serves to maintain the clutched engagement of the first 35 and the second drive member 37 during dose set and dispense operations. In its assembled state, the boss 344 acts on an inner face of the first drive member 35.

The dosing element 34 comprises an inner tubular part 349 having bone-shaped openings 345, wherein the ribs 376 of the second drive member 37 are guided. The ribs 376 abut the radial end faces 347 of the openings 345 such that a relative rotational movement of the second drive member 37 and the dosing element 34 is prevented. In an axial direction, a clearance between the axial end faces 348 of the dosing element 34 and the ribs 376 allows a limited axial movement of the dosing element 34 relative to the drive member 37. Thereby, unlocking of the first 35 and second drive member 37 for resetting the device 1 is enabled.

FIG. 7A shows a fifth embodiment of an injection device 1 having a drive unit 30 comprising a first drive member 35 and a second drive member 37. The assembly and operation of this embodiment during dose set and dispense operations is similar to that described above. The reference numerals indicate features with the same or similar function.

In this embodiment, during a dose set and dispense operation, the first 35 and second drive member 37 are locked to each other such that relative rotational and translational movements are prevented. Accordingly, during set and dispense operations, the first 35 and second drive member 37 build a drive unit 30, which is equivalent to a single drive member.

During a priming operation, the first drive member 35 is unlocked from the second drive member 37 such that a relative rotational and translational movement of the first drive member 35 relative to the second drive member 37 is allowed. In this context, "a priming operation" means that gaps between parts of the drive mechanism are removed prior to dispensing the first dose of a medicament.

During a priming operation, a dosing element 34 is in a splined engagement with the first drive member 35 such that a relative rotational movement between the first drive member 35 and the dosing element 34 is prevented and a relative translational movement is allowed. For priming the device, the dosing element 34 is rotated in the dose set direction 105 until the piston rod 5 acts on the piston 61 in the cartridge 6. At the end of the priming operation, the first 35 and the second drive member 37 are locked to each other by pushing the dosing element 34 in the distal direction 103. Thereby, also the dosing element 34 is locked to the thus established drive unit 30.

For setting a dose, the user rotates the dosing element 34 relative to the main housing 21 and for dispensing the dose, the user pusher the dosing element 34 in the distal direction 103. Thereby, a protrusion 31 located on a second spring feature on the outer surface of the second drive member 37 is guided along a track 4 formed by a ramped helical face at the distal end of an inner body 28. Simultaneously, spring means 373 on the distal end of the second drive member 37 are guided along a helical face 43 on the main housing 21.

The piston rod 5 comprises an outer female thread 53, wherein a nut 23 is threadedly engaged. Moreover, starting from its proximal end the piston rod 5 comprises a second female thread 54 wherein the first drive member 35 is threadedly engaged. The two female threads 53, 54 on the piston rod 5 are of opposite hand.

The device 1 comprises a last dose nut 24 being in splined engagement with a body insert 27 and in threaded engagement with a last dose thread 353 on the drive unit 30. As the device 1 is set, the motion of the drive unit 30 relative to the body insert 27 causes the last dose nut 24 to travel progressively down the last dose thread 353. Once the last dose has been set, the last dose nut 35 reaches the end of the last dose thread 353, prohibiting further attempts by the user to set the empty device.

FIG. 7B shows a detailed view of the drive mechanism of the injection device 1 of FIG. 7A.

At its distal end, the second drive member 37 comprises spring means 373 providing both a feedback and a non-return function. At the end of a dose setting operation, the spring means 373 ride over radial ramps 430 on the inner surface of the main housing 21. This action provides the user with feedback that a dose has been set and the shape of the ramp 430 ensures that the drive unit 30 cannot be back-rotated, effectively unsetting the dose.

During the setting action, the dosing element 34 cannot be pulled purely axially by the user due to interference between a protrusion 31 located on the drive unit 30 and the dose set section 41 of the track 4 formed by the distal edge of the body insert 27. The dose set section 41 is helical, encouraging rotation of the drive unit 30 even when under a purely axial load in the proximal direction 104. The pitch of the dose set section 41 at the track 4 is identical to the pitch of the second female thread 54 such that during setting a dose the piston rod 5 remains stationary.

Once a dose has been set, the user pushes the dosing element 34 in the distal direction 103 in order to dispense a dose. Thereby, the protrusion 31 moves along a dose dispense section 42 of the track 4. The threaded engagement between the drive unit 30 and the lead screw 5 causes the lead screw 5 to rotate and drive axially through its threaded engagement with the nut 23, thereby pushing the piston 61 in the distal direction 103.

The dose dispense section 42 comprises parts having different inclination angles to the longitudinal axis 100. When the protrusion 31 travels along the inclined dose dispense section 42 in the distal direction, the second spring feature 375 is deformed allowing a deflection of the protrusion 31. When the protrusion 31 has reached the end of the dose dispense section 42, it snaps back in an undeflected position, being driven by the tension of the second spring feature 375. This gives the user tactile and audible feedback, indicating that the dose dispense operation has been completed. After the back-deflection, the protrusion 31 abuts a stop face 410 on the subsequent dose set section 41, whereby a backward movement on the dose dispense section 42 in the proximal direction 104 is prevented.

Cut-outs 374 on the distal spring means 373 of the drive unit 30 allow the distal end of the second drive member 37 to flex axially and produce an axial spring that acts to back-off the drive unit 30, and hence the lead screw 5, from the proximal face of the piston 61 once axial load has been removed from the dosing element 34.

Other implementations are within the scope of the claims. Elements of different embodiments may be combined to form implementations not specifically described herein.

REFERENCE NUMERALS 1 injection device
  11 distal end
  12 proximal end
  103 distal direction
  104 proximal direction
2 housing
  21 main housing
  211 distal end of main housing
  214 opening
  22 cartridge holder
  23 nut
  231 engaging feature
  232 axial spline
  24 last dose nut
  242 notch
  26 back-off spring
  27 body insert
  28 inner body
3 drive member
  30 drive unit
  31 engaging feature of drive member
  310 first set of protrusions
  311 second set of protrusions
  32 inner thread of drive member
  33 stop face
  34 dosing element
  341 lug
  342 spring
  345 bone-shaped opening
  344 boss
  347, 348 stop face
  349 inner tubular part
  35 first drive member
  353 last dose thread
  354 stop face
  37 second drive member
  372 distal face
  373 first spring feature
  374 cutout
  375 second spring feature
  376 rib
  377 groove
  378 flexible arm
  379 helical sweep recess
  38 coupling means
  39 clutch
4 inner track of housing
  400 distal contact face
  401 proximal contact face
  403, 404 confining position
  40a, 40b segment
  41 dose set section
  41a path during setting a dose
  41b path during cancelling a dose
  410 stop face on dose set section
  42 dose dispense section
  42a path during dispensing a dose
  420 stop face on dose dispense section
  43 helical face
  430 radial ramp
  44 detent
  45 non-return feature
  46 insert spring
5 piston rod
  51 engaging feature of piston rod
  510 position before setting last dose
  511 position after setting last dose
  512 position after dispensing last dose
  52 flexible part
  53 outer thread of piston rod
  54 second female thread on piston rod
  56 bearing
6 cartridge
  61 piston
8 dose counter
  81 collar
  82 number sleeve
  83 thread on number sleeve
105 dose set direction
106 dose unset direction
A initial position
B stop position
C end position
D1 axial displacement of drive sleeve relative to housing
D2 axial displacement of piston rod relative to drive sleeve

The invention claimed is:

1. An injection device for administering a fixed dose of a medication comprising:
  a housing wherein a drive mechanism comprising a drive unit is at least partially enclosed; and
  a dosing element for actuating the drive unit, wherein the drive unit comprises a first drive member and a second drive member,
  wherein when a movement of the drive unit is actuated by the dosing element, during dose setting, a movement of the dosing element causes an equivalent movement of the second drive member, wherein the dose can be set by rotating the dosing element relative to the housing in the dose set direction and the dose can be dispensed by pushing the dosing element towards the housing, wherein the injection device comprises a clutch, wherein during dose setting and dose dispensing, the clutch locks the first drive member and the second drive member to each other such that relative rotational movement between the first drive member and the second drive member is prevented, wherein during a reset operation, a relative rotational movement of the first drive member and the second drive member is allowed, and wherein a set dose can be cancelled by rotating the dosing element in a dose unset direction opposite to the dose set direction.

2. The injection device according to claim 1, wherein the dosing element is fixed relative to the second drive member such that a relative rotational movement of the dosing element and the second drive member is prevented and a limited axial movement is allowed.

3. The injection device according to claim 1, wherein a single dose set direction relative to the housing is provided.

4. The injection device according to claim 1, further comprising a track, wherein the relative movement between the drive unit and the housing is defined by the track, wherein the track comprises several dose set sections and several dose dispense sections, wherein the dose dispense sections run in an axial direction and the dose set sections run helically relative to the housing.

5. The injection device according to claim 4, wherein the track is a continuous circuit.

6. The injection device according to claim 1, comprising a feedback element which gives an audible or tactile signal when one of a dose setting or a dose dispense operation has been completed.

7. The injection device according to claim 1, comprising a non-return feature which at a predefined relative position of the housing and the drive unit allows a relative movement of the drive unit and the housing in one direction and prevents a relative movement in the opposite direction.

8. The injection device according to claim 1, wherein a piston rod is provided, the piston rod acting on a piston disposed in a cartridge wherein the medication is contained, and wherein during dispensing the dose, the amount of axial displacement of the piston rod differs from the amount of axial displacement of the drive unit.

9. The injection device according to claim 8, wherein during dispensing the dose, the piston rod carries out both a rotational and a translational movement relative to the housing.

10. The injection device according to claim 8, wherein the drive unit has the shape of a sleeve which at least partially encloses the piston rod.

11. The injection device according to claim 1, comprising a stop feature which prevents one of a set operation and a dispense operation of the dosing element after the last available dose has been dispensed.

12. The injection device of claim 1 wherein the dosing element comprises a initial position and a stop position, such that to set a dose with the injection device, the user acts on the dosing element and moves the dosing element from the initial position to the stop position relative to the housing.

13. The injection device of claim 1, wherein the drive mechanism further comprises locking means configured to rotationally lock the first drive member and the second drive member during dose dispense and configured to allow unlocking for enabling a resetting of a piston rod.

* * * * *